US007160087B2

(12) United States Patent
Fathallah et al.

(10) Patent No.: US 7,160,087 B2
(45) Date of Patent: Jan. 9, 2007

(54) PUMP TUBE SET HANDLING SYSTEM (75) Inventors: Marwan A. Fathallah, Mundelein, IL (US); William C. Lindeman, Marshall, WI (US); Ami Marie Verhalen, Sun Prairie, WI (US)

(73) Assignee: Hospira, Inc., Lake Forest, IL (US)

( * ) Notice: Subject to any disclaimer, the term of this patent is extended or adjusted under 35 U.S.C. 154(b) by 555 days.

(21) Appl. No.: 10/665,776

(22) Filed: Sep. 19, 2003

(65) Prior Publication Data
US 2005/0063847 A1  Mar. 24, 2005

(51) Int. Cl.
*F04B 43/00* (2006.01)
(52) U.S. Cl. .................................. 417/477.2
(58) Field of Classification Search ................ 248/121, 248/129, 68.1
See application file for complete search history.

(56) References Cited

U.S. PATENT DOCUMENTS

| 4,406,042 A | 9/1983 | McPhee |
| 4,589,171 A | 5/1986 | McGill |
| 5,309,604 A | 5/1994 | Poulsen |
| 5,401,256 A | 3/1995 | Stone et al. |
| 5,782,805 A | 7/1998 | Meinzer et al. |
| 6,109,460 A * | 8/2000 | Herlevi et al. ........... 211/85.13 |
| 7,044,002 B1 | 5/2006 | Ericson et al. |
| 2002/0096608 A1 | 7/2002 | Cedarberg, III |
| 2002/0120229 A1 | 8/2002 | Miles, et al. |

FOREIGN PATENT DOCUMENTS

| WO | 92/17226 | 10/1992 |
| WO | 96/35472 | 11/1996 |

OTHER PUBLICATIONS

Photograph of Baxter Colleague 3 CX Pump.

* cited by examiner

*Primary Examiner*—Anthony D. Stashick
*Assistant Examiner*—Samuel E. Belt
(74) *Attorney, Agent, or Firm*—Michael R. Crabb (57) ABSTRACT A medical pump for use with a tube set having a slack portion includes a pump housing and a pumping mechanism to meter fluid into the outlet line from the inlet line. A tube snap or a tube snap set is located on the pump housing remote from the pumping mechanism to gather and hold a slack portion between first and second tube snaps. In addition or alternatively, a tube hanger can be attached to the pump housing to allow insertion of a slack portion between the tube hanger and the pump housing.

27 Claims, 5 Drawing Sheets

PUMP TUBE SET HANDLING SYSTEM

BACKGROUND OF THE INVENTION

The present invention relates to the field of medical or laboratory equipment. More particularly, this invention relates to a means of securing slack portions of tube set lines or other lines to a medical device, including but not limited to a medical pump.

Modern medical care often involves the use of medical pump or other devices to deliver fluids and/or fluid medicine to patients. Medical pumps are typically used to meter fluid through a tube set and into a patient.

Tube sets typically have an inlet line portion transporting fluid from a fluid bag to the medical pump, and an outlet line portion transporting fluid from the medical pump to a patient. As tube sets come in many designs, the length of inlet and outlet line portions are not uniform, and often vary from use to use. Further, the distance from the fluid bag to the medical pump and the distance from the medical pump to the patient are also variable. Due to these variations in line length as well as distance between fluid bag, medical pump, and patient, there is typically a slack portion of line formed in one or more of the inlet and outlet line portions.

Whether slack portions occur in the inlet line portion or the outlet line portion, they are at best inconvenient and at worst detrimental to the proper administration of fluid to the patient. The fluid bag, tube set and medical pump are often attached to a wheeled pole stand and transported to a new location. During transport, the slack portion of the outlet line portion can cause an adaptor end of the tube set to drag on the floor, contaminating the previously sterilized tube set. Where more than one tube set is in use, for example in a programmable multiple channel medical pump, the slack portions can cause a user to lose proper tube set/channel correspondence, resulting in incorrect administration of fluid to the patient. Further loose slack portions create a tangling and/or tripping hazard for those persons moving about the tube set.

It is therefore a principal object of this invention to provide means securing slack portions of tube set lines to a medical pump or similar device.

A further object of the this invention is the provision of a means for securing slack portions of tube set lines to a medical pump such that a generally vertical flow pattern is easily maintained.

A further object of the this invention is the provision of a means for securing slack portions of tube set lines to a medical pump such that flow path/channel correspondence is visually readily apparent to a user.

A further object of the this invention is the provision of a means for looping and securing slack portions of tube set lines to a medical pump such that the chances of folds, kinks, and occlusions in the lines are reduced.

A further object of the this invention is the provision of a means for securing slack portions of tube set lines to the handle of a medical pump.

A further object of the this invention is the provision of a means for securing slack portions of tube set lines to a cleat or tube hanger located on the front face of a medical pump.

These and other objects will be apparent to those skilled in the art.

SUMMARY OF THE INVENTION

The present invention relates to the field of medical or laboratory equipment. More particularly, this invention relates to a means of securing slack portions of tube set lines or other similar elongated lines to a medical device, including but not limited to a medical pump.

A medical device, such as a pump for use with a tube set having inlet, outlet, slack and operative line portions is disclosed. The pump includes a pump housing and a pumping mechanism to meter fluid into the outlet line portion from the inlet line portion. In one embodiment, at least one tube snap located on the pump remote from the pumping mechanism is adapted to permit insertion and removal of a slack portion of the tube set. In another embodiment, a tube snap set including at least one tube snap located on the pump remote from the pumping mechanism is adapted to permit insertion and removal of a slack portion of the tube set. Preferably the tube snap set includes first and second tube snaps defined by a pair of grooves. At least one of the tube snap grooves preferably extends generally parallel to the pumping mechanism so that tube set correspondence with the pumping mechanism is easily discernible to the user. The tube snap set gathers, holds and makes adjustable lengthwise a slack portion of the inlet line portion between first and second tube snaps.

A tube hanger cleat is attached to the pump housing to permit a user to hang a slack portion thereon. Preferably the cleat is spaced from the pump housing sufficiently to allow insertion of a portion of the line between the tube hanger cleat and the pump housing. More preferably the cleat can be utilized for gathering and holding a slack portion of the line between the tube hanger cleat and the pump housing. The cleat has first and second side hooks extending transversely of the main arm. The first and second side hooks can be utilized to gather and hold a slack portion of one tube set or slack portions of two separate tube sets between the tube hanger cleat and the pump housing.

DETAILED DESCRIPTION OF THE PREFERRED EMBODIMENT

In the figures, as well as in the description that follows, similar features are identified by similar reference numerals.

Figure 1:
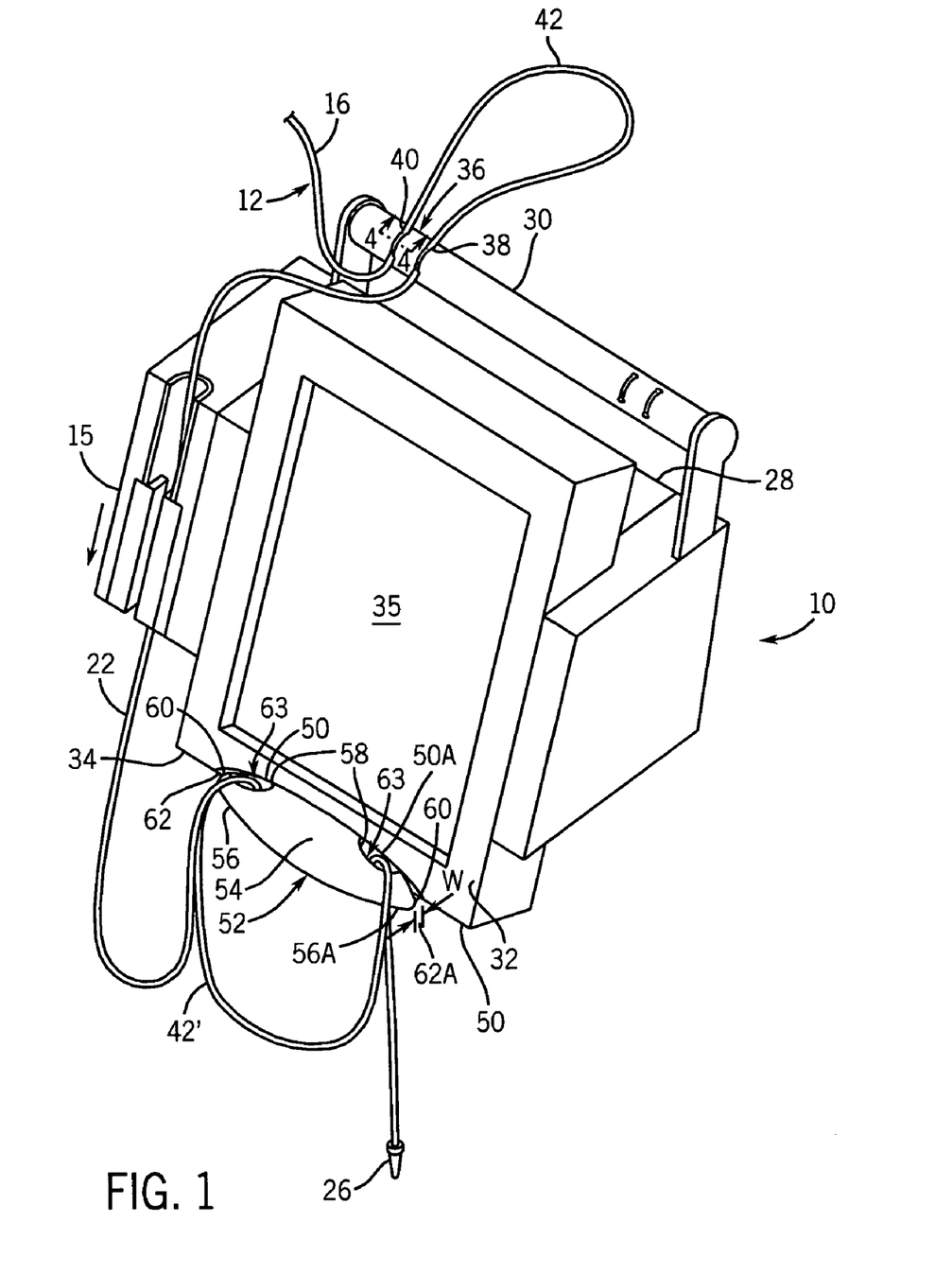
FIG. 1 is a perspective view of a single channel medical pump according to the present invention.

Referring to FIG. 1, a single channel medical pump 10 according to the present invention is shown. The term "medical pump" as used herein includes but is not limited to enteral feeding pumps, parenteral or intravenous (IV) infusion pumps, syringe pumps or any single or multiple channel fluid pumping device for the delivery of fluids to a patient through tubing.

Figure 2:
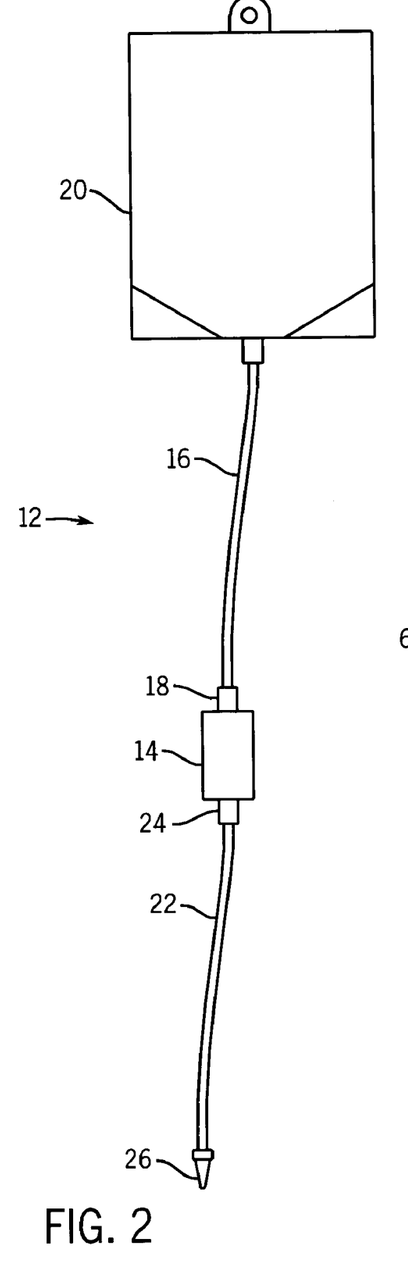
FIG. 2 is a front view of a tube set for use with a pump according to the present invention.

With additional reference to FIG. 2, the pump 10 is typically used in connection with one or more tube sets 12 for delivering a fluid to a patient. It will be appreciated that the pump 10 and tube set 12 may include fewer or more components than those shown in FIGS. 1 and 2. However, the tube set is not the focus of the present invention and it is not necessary that all tube set components be shown in order to disclose an illustrative embodiment for practicing the present invention.

In some cases, such as where the pump is of the type known as a cassette pump, the tube set 12 includes a cassette 14 as operative line portion (hereinafter "operative portion"). The tube set 12 is typically used only for a single patient and for one fluid delivery cycle. The operative portion of the tube set 12, more particularly the cassette 14 in the illustrated embodiments, is inserted into or received by a pumping mechanism or channel 15.

The pumping mechanism 15 can be associated with a pump housing 28 of the pump in a variety of ways. The pumping mechanism 15 can be attached to the pump housing 28, housed within it, directly or indirectly connected to it, or even remotely connected by wire or wirelessly with the pump housing 28. The pumping mechanism 15 controls or meters the flow of fluid in a fluid flow direction through the tube set 12 by receiving and acting on the operative portion (cassette 14) of the tube set 12. Although other orientations are possible, for greatest ease of channel/tube set identification, the normal orientation of the pump 10, pumping mechanism 15, tube set 12, and thus the fluid flow direction is preferably generally vertical as indicated by the arrow in FIG. 1. One skilled in the art will appreciate that the present invention can also be utilized with other types of conventional pumping mechanisms that use or act upon tubing, including but not limited to peristaltic, syringe, and blade pumps.

An inlet line portion 16 comprising a tube 17 is connected in fluid communication between an inlet port 18 of cassette 14 and a fluid source, such as a fluid container or bag 20. In non-cassette type pumps, the inlet line portion 16 is defined as the portion between the fluid bag or source and the pumping mechanism, i.e., upstream of the pumping mechanism. The fluid source, inlet portion and pumping mechanism can be combined into a single device such as a syringe. Similarly, an outlet line portion 22 comprising a tube 17 is connected in fluid communication between an outlet port 24 of cassette 14 and an adapter end 26 of the tube set 12. In non-cassette type pumps, the outlet line portion 22 is defined as the portion downstream of the pumping mechanism. Of course, the operative portion is the portion of the tube set being acted upon by the pumping mechanism. While the invention has been described as for use with a tube set 12 having an inlet line portion 16 and an outlet line portion 22 connected to an operative line portion comprising a cassette 14, the present invention is also adapted for use with tube sets having no cassette, where the inlet and outlet line portions 16 and 22 are of unitary construction or connected by other means.

Referring to FIG. 1, the medical pump 10 includes a pump housing 28 having a handle portion 30 permitting a user to grasp the pump 10 by the handle portion 30. The pump housing 28 includes a front wall 32, a bottom wall 34 and a user interface screen 35 on the front wall 32. A tube snap set 36 is located on the pump housing 28, preferably remote from the pumping mechanism 15, and more preferably on the handle portion 30 near the pumping mechanism 32. The tube snap set 36 is adapted to permit insertion and removal of a slack portion of the tube set.

The tube snap set 36 includes a first tube snap 38 that allows a user to removably secure the inlet line 16 to the pump 10 at a location remote from the first pumping mechanism 32. A second tube snap 40 is located spaced apart from and adjacent to the first tube snap 38 on the handle portion 30. The first and second tube snaps 38 and 40 form the tube snap set 36. The tube snap set 36 allows a user to gather and retain a slack portion 42 of the inlet line 16 to the pump 10 between the first tube snap 38 and the second tube snap 40. As shown, the slack portion 42 may be formed into a loop when secured. Advantageously the tube snap set 36 also allows the length of the loop in the slack portion 42 to be adjusted. The tube snap set 36 slidably secures this loop to the pump 10 and prevents the loop from unraveling. The user can adjust the length of the slack portion 42 by pulling longitudinally or axially on the tube set 12 at or adjacent to the slack portion 42. Thus, the tube snap set 36 is adapted to receive and slidably retain a slack portion 42 of the tube set 12 between the first tube snap 38 and the second tube snap 40 such that the retained slack portion 42 is adjustable in length.

Referring to FIGS. 1 and 4A–4C, the first and second tube snaps 38 and 40 are each formed as an elongated groove 44 in the handle portion 30. Preferably each groove 44 of the pair of the grooves extends transversely across the handle portion 30, and more preferably approximately perpendicular to the central longitudinal axis of the handle portion 30. Thus, one or more of the grooves 44 extends generally parallel to the fluid flow direction through the pumping mechanism 15. The groove 44 has an opening 46 that permits the insertion and removal of the tube 17 of the inlet line portion 16. A pair of opposing tapered edges 48 is located about the opening 46 and secures the slack portion 42 to the pump 10 once the tube 17 is inserted into the groove 44. Preferably the opening 46 of the groove 44 is approximately the same diameter as the tube 17 and is C-shaped, surrounding more than 180 degrees of the circumference of the tube 17, so that the user manually inserts or snaps the slack portion 42 of the tube set 12 into the groove 44, where it is retained unless pulled out by the user. The tube 17 of the tube set 12 resiliently deforms as it is inserted or withdrawn from the groove opening 46. The groove 44, opening 46, the tapered edges 48, and the gap therebetween are configured (size, shape, and radiuses) so that insertion and withdrawal forces required are well within the capabilities of most users and the tube 17 is firmly retained without permanently deforming the tube 17. Permanent deformation of the tube 17 could adversely affect its flow characteristics and the operation of the pump 10

The illustrated embodiments show the tube snap set 36 being used to retain a slack portion of the inlet line portion 16, but one skilled in the art will appreciate that a slack portion of the outlet line portion 22 could be similarly retained if desired. In other words, the slack portion can occur in the inlet line portion 16 or the outlet line portion 22. Furthermore, a single tube snap or groove formed in the pump housing remote from the pumping mechanism can be utilized to obtain most of the benefits of the present invention, particularly if the groove is generally parallel to the fluid flow direction. More preferably the groove should be located above and in general vertical alignment with the pumping mechanism.

Figure 3:
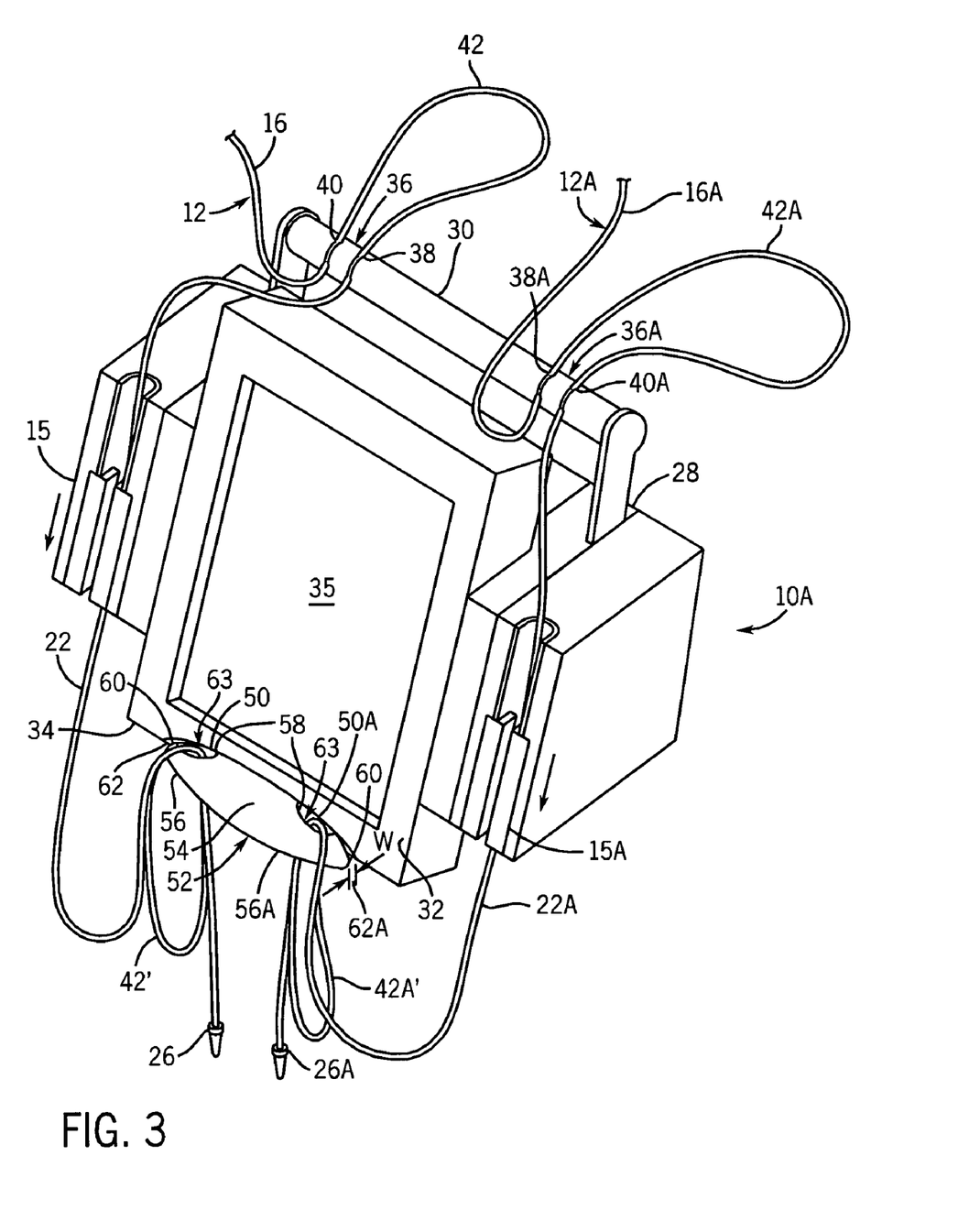
FIG. 3 is a perspective view of a dual channel medical pump according to the present invention, and shows the tube snaps and tube hanger being associated with multiple tube sets.
Figure 4A:
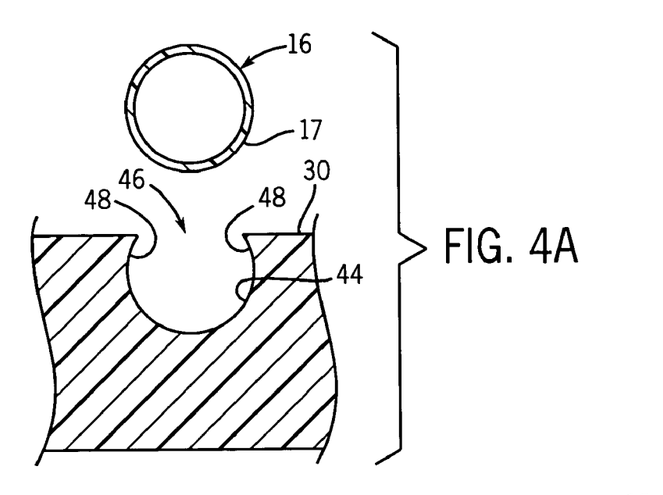
FIGS. 4A–4C are partial sectional views of a tube set snap of the present invention taken along line 4—4 of FIG. 1, illustrating the slack portion of the tube set being inserted or snapped into the tube snap.
Figure 4B:
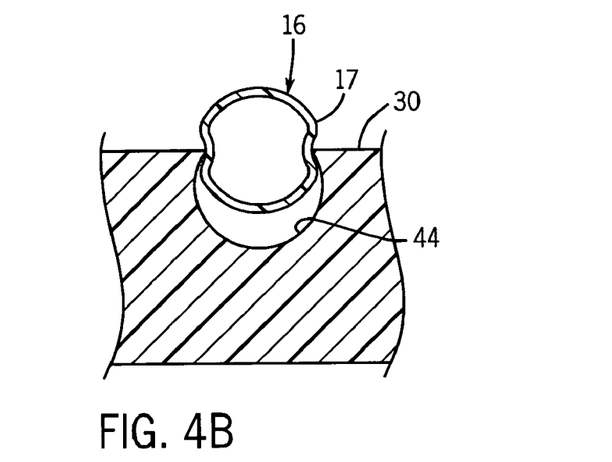
Figure 4C:
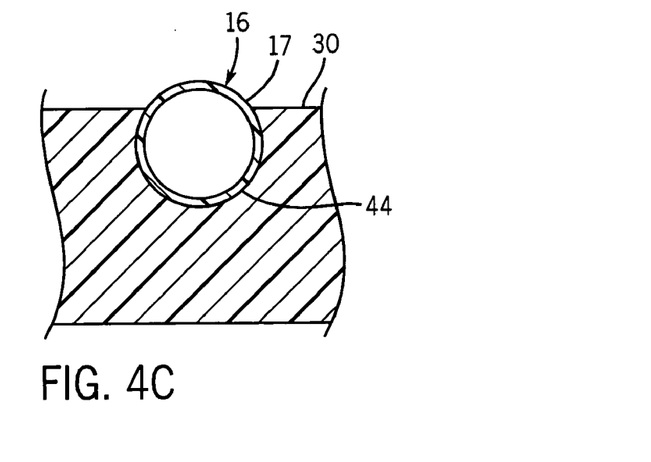

FIG. 3 shows that multiple pumping mechanisms, such as first and second pump mechanisms 15 and 15A, can be associated with the pump housing 28. The pumping mechanisms 15, 15A each receive a cassette 14, 14A (not shown) of a tube set 12, 12A and act on the cassette 14, 14A to meter fluid from the inlet line portion 16, 16A through the cassette 14, 14A, and into the outlet line portion 22, 22A in the fluid flow direction. While the pump 10A is shown with two pumping mechanisms 15 and 15A, one skilled in the art could easily adapt the invention to pumps having additional pumping mechanisms by utilizing the concepts disclosed herein. In the embodiment shown, there is a first tube snap set 36 and a second tube snap set 36A provided above the first and second pumping mechanisms 15 and 15A respectively. Like the first tube snap set 36, the second tube snap set 36A includes at least one, more preferably several, and most preferably two tube snaps 38A, 40A. FIG. 3 illustrates how the pairs of tube snaps 38, 40, 38A, 40A are generally aligned above the respective pumping mechanisms 15, 15A, which leaves the user interface screen 35 on the front wall 32 of the pump housing 28 unobstructed. FIG. 3 also shows that the tube snaps 38, 40, 38A, 40A are closely adjacent to each other (i.e., juxtapositioned) within their respective pairs such that either the inboard snap 38, 38A or the outboard snap 40, 40A can be utilized for the part of the inlet portion 16, 16A closest upstream of the pumping mechanism 15, 15A. Due to the tube snap sets 36 and 36A being spaced apart, positioned near, and more preferably generally vertically aligned with their respective pumping mechanisms 15 and 15A, once tube sets 12, 12A are secured to the respective tube snap sets 36 and 36A, user confusion over associating the proper tube set with the proper channel or pumping mechanism 15, 15A is reduced.

Referring to FIGS. 1 and 3–7, a housing recess 50, 50A forms part of the pump housing 28. The housing recess 50, 50A preferably extends inwardly from the front wall 32 of the pump housing 28. More preferably the housing recess 50, 50A extends from the front wall 32 to the bottom wall 34 of the pump housing 28, with the depth of the recess 50, 50A gradually increasing toward the bottom wall 34.

Figure 5:
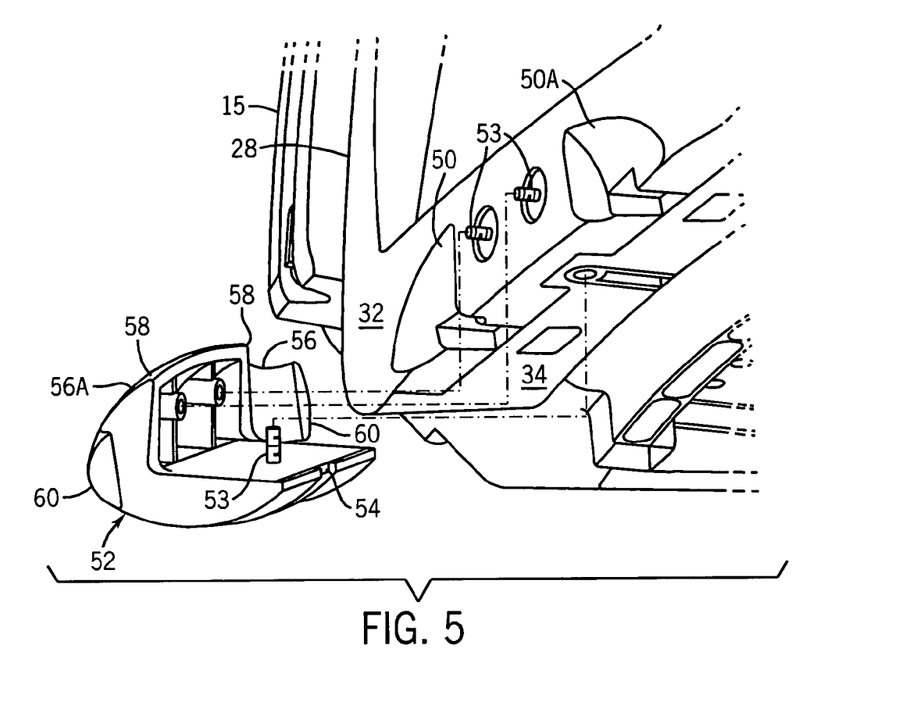
FIG. 5 is a partial exploded perspective view of the tube hanger and pump housing of this invention.
Figure 6:
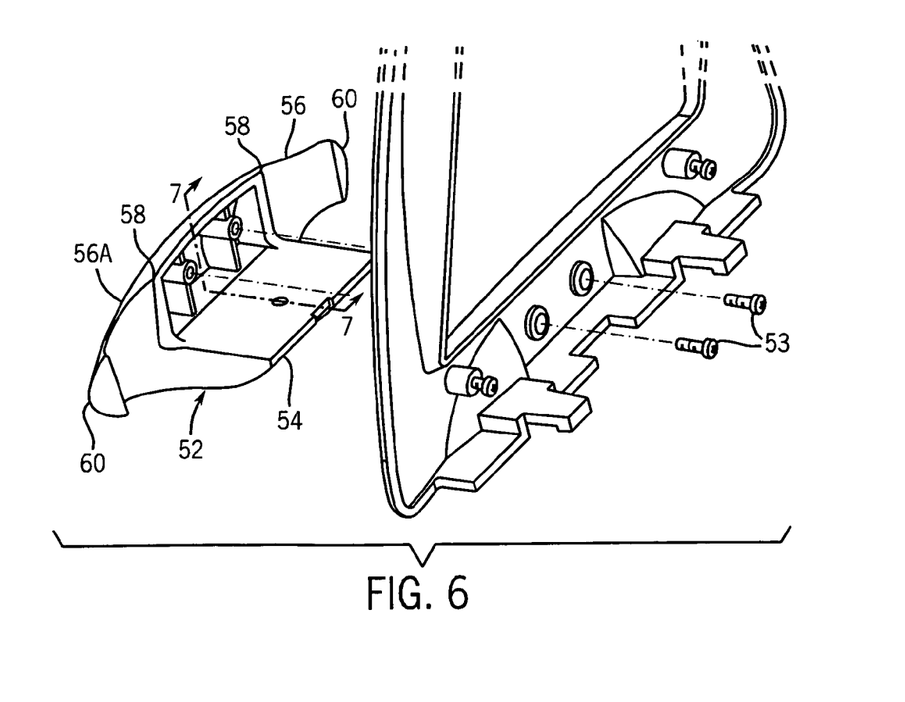
FIG. 6 is another partial exploded perspective view of the tube hanger and pump housing of this invention.
Figure 7:
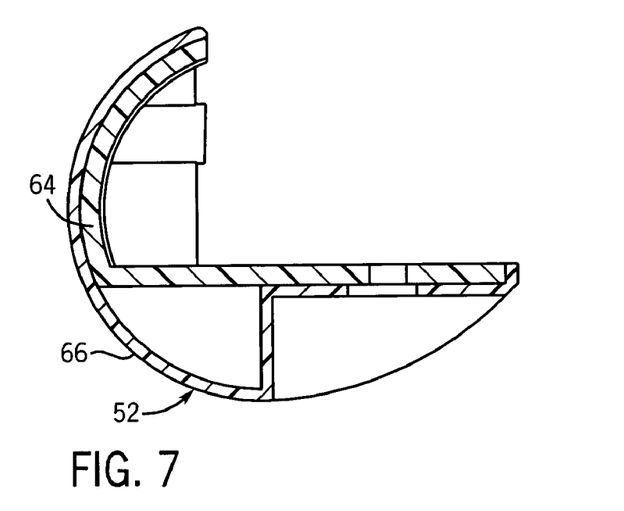
FIG. 7 is a cross sectional view of the tube hanger taken along line 7—7 in FIG. 6.

A tube hanger 52 is attached to the pump housing 28 to receive and removably secure a slack portion 42' of the tube set 12 to the pump 10. The tube hanger 52 includes a main arm 54 extending outwardly from the pump housing 28 and at least one hook 56, or more preferably a pair of oppositely extending hooks 56, 56A, extending laterally from the main arm 54 in spaced relation to the pump housing 28 so as to receive, hang and hold the slack portion 42' between the hook 56 and/or 56A and the pump housing 28. Preferably the housing recess 50, 50A is located behind and registered with the hook 56 or hooks 56, 56A of the tube hanger 52.

Each hook 56, 56A has a proximate end 58 attached to the main arm 54 and a distal end 60 positioned relative to the pump housing 28 so as to define an insertion gap 62, 62A. The gap 62, 62A is configured or adapted to permit a slack portion 42' of the tube set 12 to be freely, or more preferably with some light manual force (i.e., "snappingly"), passed therethrough without permanent deformation of the tube set. Preferably each hook 56, 56A is constructed such that the insertion gap 62, 62A opens into a tube retention space 63 between the hook and the pump housing 28. The tube retention space 63 increases in width and then decreases in width between the distal end 60 of the hook and the proximate end 58 of the hook. Of course, at its widest point the tube retention space 63 is preferably considerably wider than the diameter of the tube. This helps prevent permanent tube deformation and allows multiple tubes or loops of tubing to be hung from the hook 56 or hooks 56, 56A.

The hooks 56, 56A preferably extend horizontally when the pump 10 is in the orientation shown. Main arm 54 of the tube hanger 52 can be rigidly attached to any readily accessible portion of the pump housing 28. For example, the main arm 54 of the tube hanger 52 can be attached to a bottom wall 34, the front wall 32 below the user interface screen 35, or more preferably both the front wall 32 and the bottom wall 34 of the pump housing 28. The latter configuration is illustrated in FIG. 5. The tube hanger 52 can be attached to the pump housing 28 by fastening means on the housing 28, the hanger 52, or both. The fastening means may include any suitable conventional fastener 53, including but not limited to screws, rivets, heat welding or staking, mating recesses and detents, or snaps.

As best understood in view of FIGS. 5–7, the tube hanger 52 is preferably substantially smooth, at least semi-rigid, and constructed of a durable polymer plastic material. The tube hanger 52 can be formed, molded, or coated with a resiliently flexible material with some non-slip frictional surface characteristics. Most preferably the tube hanger comprises a hard thermoplastic substrate 64 that is over molded, coated or co-extruded with a layer 66 of softer material having elastomeric properties.

The substrate material may include, but is not limited to, copolymers of acrylonitrile, butadiene, and styrene (ABS) or polycarbonate, acrylonitrile, butadiene, and styrene (PC/ABS). Preferably the pump housing 28 is formed of a similar material, which facilitates heat welding or heat staking of the tube hanger 52 to the pump housing 28.

The over molded layer 66 may include, but is not limited to, synthetic rubbers such as neoprene or sanoprene. The flexibility and resiliency of the over molded layer 66 facilitates the passage of the slack portion 42' of the tube set 12 through the gap 62 or 62A without damage. Furthermore, the over molded layer 66 allows the width W of the gap 62 or 62A at the distal end 60 to be set slightly smaller than the tube diameter so that the user must forcibly push or pull (i.e., snap) the slack portion 42' through the gap 62 or 62A during insertion or withdrawal. This improves retention of the slack portion 42' on the tube hanger 52 by inhibiting inadvertent withdrawal. In addition to the geometry of the tube hanger 52, the non-slip material characteristics of the over molded layer 66 help hold the loop in the slack portion 42' in place.

The tube hanger 52 extends outwardly from the pump housing 28 and is adapted to receive, hang and removably secure a slack portion 42' to the pump 10 at a location remote from the pumping mechanism 15. FIG. 1 shows how a slack portion 42' of a single tube set 12 can be looped and hung from or secured to the tube hanger 52, whereas FIG. 3 shows how the tube hanger 52 can be used to hang or secure slack portions 42', 42A' of two separate tube sets 12 simultaneously. In FIG. 3, a dual channel pump 10A has two pumping mechanisms 15, 15A and corresponding tube sets 12, 12A associated therewith. In the embodiment shown the tube sets 12, 12A are identical, but this need not be the case.

The first side hook 56 allows a user to gather, hang and hold a slack portion 42' of the outlet line 22 of the first tube set 12 within the tube retention space 63 between the first side hook 56 and the pump housing 28 at the housing recess 50. As shown the slack portion 42' of the outlet line 22 of the second tube set 12A may be formed into a loop when secured, the tube hanger 52 secures this loop to the pump 10 and usually prevents the loop from unraveling. The second side hook 56A allows a user to gather and hold a slack portion 42A' of the outlet line 22A within the tube retention space 63 between the second side hook 56A and the pump housing 28 at the housing recess 50A. As shown the slack portion 42A' may be formed into a loop when secured, the tube hanger 56A secures this loop to the pump 10 and usually prevents the loop from unraveling. However, if adequate tube retention space is provided, the length of the loops in the slack portions 42', 42A' can be adjusted by the user pulling longitudinally or axially on the tube.

Due to the first and second side hooks 56, 56A being positioned near their respective pumping mechanisms 15, 15A, once tube sets 12, 12A are secured to their respective first and second side hooks 56 and 56A, user confusion over associating the proper tube set with the proper channel or pumping mechanism is reduced.

FIGS. 1 and 3 illustrate that the tube hanger 52 can be utilized according to at least two different methods or arrangements. First, a slack portion 42' can be wrapped around both side hooks 56, 56A as shown in FIG. 1. This reliably secures the slack portion 42' and is the preferred method or arrangement when the pump 10 has a single channel or pumping mechanism 15. A second method or arrangement is shown in FIG. 3 and is preferred for a pump 10A that has dual channels or pumping mechanisms 15, 15A. One or more loops are formed in the slack portions 42', 42A'. Then the loops of the slack portions 42', 42A' are inserted through the respective gaps 62, 62A at the opposite ends of the tube hanger 52. This allows the tube hanger 52 to hold the slack portions 42', 42A' of two separate tube sets 12, 12A in a way that automatically spaces them apart by the width of the main arm 54 such that they do not become crossed or confused easily.

It also can be seen that both the tube snaps and the tube hanger provide means for looping and securing slack portions of tube set lines to a medical pump such that the chances of folds, kinks, and occlusions in the lines are reduced.

It is therefore seen that the present invention provides means for securing slack portions of tube set lines to a medical pump and will achieve at least all of its stated objectives.

What is claimed is:

1. A medical pump for use with a tube set having inlet, outlet, slack and operative line portions, comprising:
   a pump housing;
   a pumping mechanism associated with the pump housing adapted to receive an operative line portion of a tube set and to pump fluid from an inlet line portion and into an outlet line portion of the tube set; and
   a tube snap set adapted to permit forcible insertion and removal of a slack portion of the tube set
   wherein the tube snap set includes an inboard tube snap and a outboard tube snap non-coaxial with and radially spaced from the inboard tube snap, the tube snap set being adapted to receive and slidably retain a slack portion of the tube set between the inboard tube snap and the outboard tube snap such that the retained slack portion is adjustable in length.

2. The medical pump of claim 1, wherein the tube snap set is located remote from the pumping mechanism and on a handle portion of the pump housing.

3. The medical pump of claim 1, wherein the pump housing has a pair of laterally spaced elongated grooves formed therein that defines the inboard and outboard tube snaps, each groove has a pair of opposing tapered edges end an opening extending therebetween.

4. The medical pump of claim 3, wherein the opening of the groove is C-shaped.

5. The medical pump of claim 3, wherein the pumping mechanism is adapted to pump fluid in a fluid flow direction and at least one of the grooves extends generally parallel to the fluid flow direction.

6. The medical pump of claim 5, wherein both of the grooves extend generally parallel to the fluid flow direction.

7. The medical pump of claim 5, wherein the fluid flow direction is generally vertical.

8. The medical pump of claim 5, wherein the grooves are located on a handle portion of the pump housing.

9. The medical pump of claim 1, further comprising a tube hanger attached to the pump housing to receive and removably secure a slack portion of the tube set to the pump.

10. The medical pump of claim 9, wherein the tube hanger includes a main arm extending outwardly from the pump housing and at least one hook extending laterally from the main arm in spaced relation to the pump housing so as to receive and hold a slack portion between the hook and the pump housing.

11. The medical pump of claim 10, wherein the main arm of the tube hanger is attached to a bottom wall of the pump housing.

12. The medical pump of claim 10, wherein the main arm of the tube hanger is attached to a front wall of the housing.

13. The medical pump of claim 10, wherein the pump housing includes a housing recess located behind the hook of the tube hanger.

14. The medical pump of claim 10, wherein the housing recess extends from a front wall of the pump housing to a bottom wall of the pump housing.

15. The medical pump of claim 10, wherein the tube hanger includes two hooks extending in opposite directions from the main arm, each hook having a proximate end attached to the main arm and a distal end positioned relative to the pump housing so as to define an insertion gap adapted to permit a slack portion of the tube set to be snappingly passed therethrough.

16. The medical pump of claim 15, wherein the insertion gap opens into a tube retention space defined between the pump housing and the hook, the hook being constructed so that the tube retention space increases in width and then decreases in width between the distal end of the hook and the proximate end of the hook.

17. The medical pump of claim 1, wherein the tube snap set is located above and in generally vertical alignment with the pumping mechanism.

18. The medical pump of claim 17, wherein the pumping mechanism is a cassette pump.

19. A medical pump for use with a tube set having inlet, outlet, slack and operative line portions, comprising:
    a pump housing including a user interface screen thereon;
    a pumping mechanism associate with the pump housing and adapted to receive an operative line portion of a tube set and to pump fluid from an inlet line position and into an outlet line portion; and
    a tube hanger attached to a wall of the pump housing below the user interface screen and adapted to receive and removably secure a slack portion of line to the pump at a location remote from the pumping mechanism.

20. The medical pump of claim 19, wherein the tube hanger includes a main arm extending outwardly from the pump housing and at least one hook extending laterally from the main arm in spaced relation to the pump housing so as to receive and hold a slack portion between the hook and the pump housing.

21. The medical pump of claim 20, wherein the pump housing has a front wall that includes the user interface screen and the main arm of the tube hanger is attached to the front wall of the pump housing below the user interface screen.

22. The medical pump of claim 20, wherein the pump housing includes a housing recess located behind the hook of the tube hanger.

23. The medical pump of claim 22, wherein the housing recess extends from a front wall of the pump housing to a bottom wall of the pump housing.

24. The medical pump of claim 20, wherein the tube hanger includes two hooks extending in opposite directions from the main arm, each hook having a proximate end attached to the main arm and a distal end positioned relative to the pump housing so as to define an insertion gap adapted to permit a slack portion of the tube set to be snappingly passed therethrough.

25. The medical pump of claim 24, wherein the insertion gap opens into a tube retention space defined between the pump housing and the hook, the hook being constructed so that the tube retention space increases in width and then decreases in width between the distal end of the hook and the proximate end of the hook.

26. A medical pump for use wit a tube set having inlet outlet, slack and operative line portions, comprising:
   a pump housing;
   a pumping mechanism associated with the pump housing adapted to receive an operative line portion of a tube set and to pump fluid from an inlet line portion and into an outlet line portion of the tube set; and
   a tube snap set adapted to permit insertion and removal of a slack portion of the tube set;
   wherein the tube snap set is located remote from the pumping mechanism and on a handle portion of the pump housing.

27. A medical pump for use with a tube set having inlet, outlet, slack and operative line portions, comprising:
   a pump housing;
   a pumping mechanism associate with the pump housing and adapted to receive an operative line portion of a tube set and to pump fluid from an inlet line portion and into an outlet line portion; and
   a tube hanger attached to the pump housing and adapted to receive and removably secure a slack portion of line to the pump at a location remote from the pumping mechanism;
   wherein the tube hanger includes a main arm extending outwardly from the pump housing and at least one hook extending laterally from the main arm in spaced relation to the pump housing so as to receive and hold a slack portion between the hook and the pump housing;
   wherein the at least one hook has a proximate end attached to the main arm and a distal end positioned relative to the pump housing so as to define an insertion gap that permits a slack portion of the tube set to be snappingly passed therethrough.

* * * * *